Figure 1:
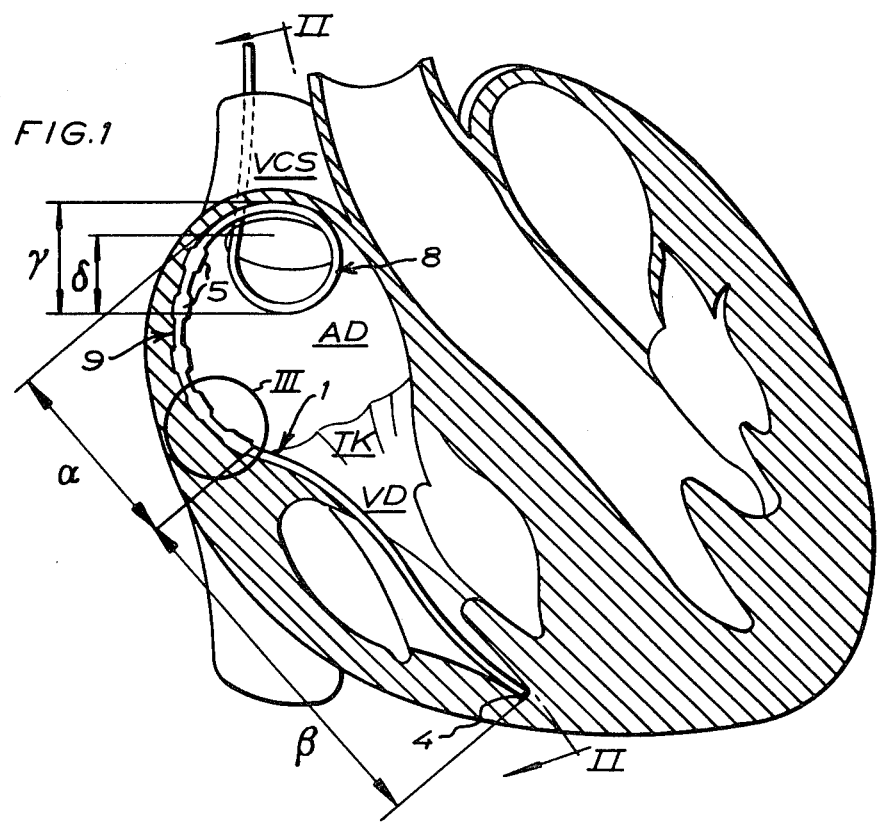

United States Patent [19]

Reenstierna

[11] 4,401,126
[45] Aug. 30, 1983

[54] ENDOCARDIAL, IMPLANTABLE LEAD FOR PACEMAKER

[76] Inventor: Bertil Reenstierna, Borgeby 11, S-230 50 Bjärred, Sweden

[21] Appl. No.: 237,157
[22] PCT Filed: Jun. 13, 1980
[86] PCT No.: PCT/SE80/00170
 § 371 Date: Feb. 13, 1981
 § 102(e) Date: Feb. 13, 1981
[87] PCT Pub. No.: WO80/02801
 PCT Pub. Date: Dec. 24, 1980
[51] Int. Cl.³ .............................................. A61N 1/04
[52] U.S. Cl. ................................. 178/784; 128/419 P
[58] Field of Search .................... 128/419 P, 784, 785, 128/786

[56] References Cited
U.S. PATENT DOCUMENTS 3,729,008  4/1973  Berkovits .................... 128/419 P
3,939,843  2/1976  Smyth ........................ 128/419 P
4,057,067  11/1977  Lajos ......................... 128/419 P
4,154,247  5/1979  O'Neill ....................... 128/419 P Primary Examiner—William E. Kamm
Attorney, Agent, or Firm—Karl W. Flocks; Sheridan Neimark

[57] ABSTRACT

An endocardial, implantable lead (1) for connection with an implantable pacemaker comprises an electrical conductor (3) adapted, via at least one electrode (5) connected thereto and in contact with the inner wall of the right auricle (AD), to transfer stimulating pulses to the heart or collect heart pulses from the heart. The lead (1) is spring-biased along a predetermined portion (8, 9) of its length to assume a curved shape ($\alpha$), which predetermined portion contains the electrodes (5) and is adapted to be located in the heart auricle and bear against the inner wall thereof. A withdrawable relatively stiff wire (10) is adapted for straightening of the curved shape of the predetermined portion (8, 9) before and during insertion of the electrodes (5) in the auricle.

1

11 Claims, 3 Drawing Figures

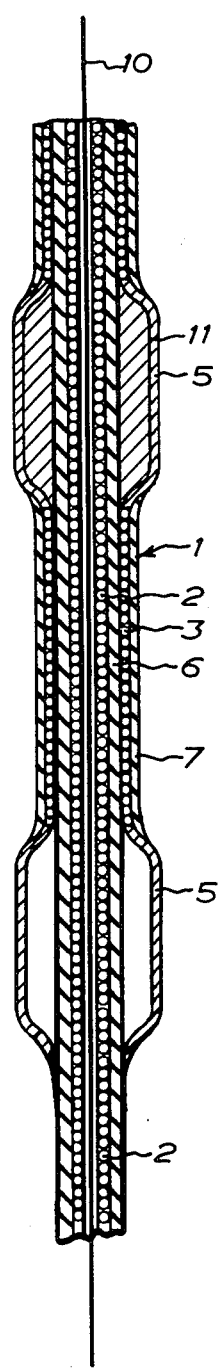

ENDOCARDIAL, IMPLANTABLE LEAD FOR PACEMAKER

This invention relates to an endocardial, implantable lead for connection with an implantable pacemaker.

Many leads of this kind have become known for transferring stimulating pulses from a pacemaker box to the heart or for supplying the heart's own pulses to the pacemaker box.

To establish reliable contact between the auricle electrode and the cardiac tissue there have been developed a great many means provided on or in the lead and being of the type of hooks, barbs and screws. These means are adapted to be actuated from outside the patient's body so as to penetrate into the cardiac tissue and carry along the electrode, thereby establishing contact with the cardiac tissue.

The disadvantages associated with such means are that they can easily damage the cardiac tissue and can also easily come loose so that the requisite reliable contact with the cardiac tissue is jeopardized.

Prior art for example, shows a curved portion of a lead having electrodes to contact the cardiac tissue. The curved portion may consist of a loop, the general plane of which includes the lead portions connected to the loop. These types of lead portions act like a leaf spring under the compressions and expansions of the heart, thereby creating a risk for injuring the heart inner wall, especially at the tip portion of the lead in contact with the heart ventricle.

The object of the invention is to provide an endocardial, implantable lead of this type, which without the aid of tissue-tearing means can establish good contact between the auricle electrode and the cardiac tissue.

This object is realized in accordance with the present invention by means of a lead of the type described in the foregoing and possessing the characteristic features that appear from the appended claims.

The invention will be described in greater detail below with reference to the accompanying drawings.

Figure 2:
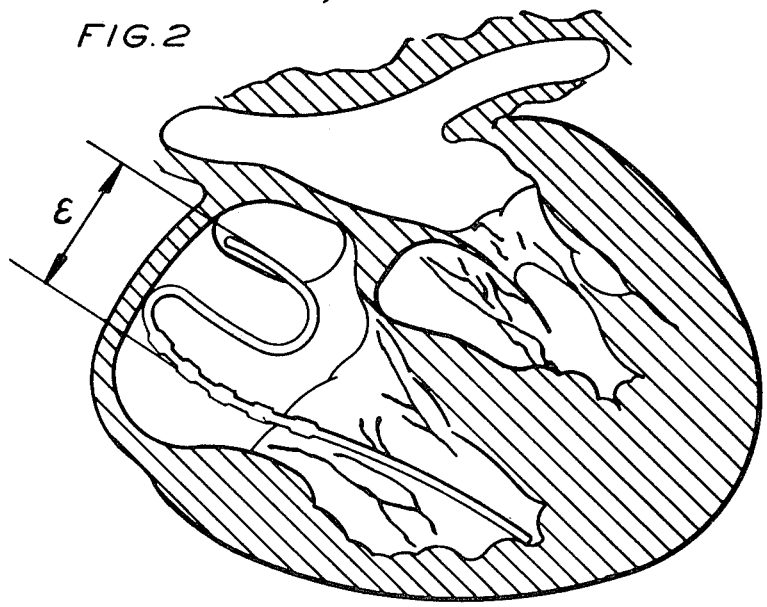

FIG. 1 is a longitudinal section of a human heart with a lead according to the invention implanted therein, FIG. 2 is a section on line II—II in FIG. 1, and FIG. 3 is an enlarged view of a portion (III in FIG. 1) of the lead.

FIG. 1 shows an intravascular endocardial lead 1 which is implanted in a human heart via a punctured body vessel (not shown), such as one jugular vein, and via the superior vena cava VCS (vena cava superior). It is now referred to FIG. 3 where a portion III in FIG. 1 of the lead is shown in enlargement. The lead 1 comprises two flexible helical concentrically arranged conductors 2 and 3 of some metal or metal alloy conventional for the purpose contemplated, such as a platinumiridium alloy. At its distal end the inner conductor 2 is connected to an electrode 4 in contact with the apex of the right heart ventricle VD (ventriculus dexter). At and adjacent to its distal end which is upstream of the distal end of the inner conductor 2, the outer conductor 3 is connected to auricle electrodes 5 which are spaced apart in the longitudinal direction of the lead 1 and are in contact with the inner wall, the endocardium, of the right auricle AD (atrium dexter) to receive heart pulses.

At their proximal ends the conductors 2, 3 are connectible to an implantable heart stimulating circuit adapted, in response to the heart pulses received from the electrodes 5, to generate heart stimulating pulses and transfer these generated heart stimulating pulses via the electrode 4 to the right ventricle VD. The lead 1 illustrated is thus adapted for auricle controlled heart stimulation of a human heart with partial or total AV-block.

Sheaths 6, 7 are formed about the conductors 2, 3. The inner sheath 6 embraces the inner conductor 2 from the proximal end thereof to the electrode 4 and separates said inner conductor from the outer conductor 3. The outer sheath 7 consists of a continuous portion extending from the proximal end of the outer conductor 3 to the first auricle electrode 5, as viewed from said proximal end, and of several spaced apart successive portions embracing the outer conductor 3, between which portions the other auricle electrodes 5 protrude. The last-mentioned electrodes are in the form of rings which are electrically connected to the outer conductor 3, for example by soldering, at their upper and lower edges and are made from a tissue-compatible material, such as the same platinum/iridium alloy as the conductors 2, 3.

The sheaths 6, 7 are made from a tissue-compatible, electrically insulating elastomer, such as a silicon rubber. The inner sheath 6, when being moulded into a tube over that part of its length which is to lie in the auricle AD, has been given the shape of a loop or a one-turn coil 8 and a curved portion 9 connecting onto said coil and containing the auricle electrodes 5. The coil 8 can be a right-hand turn, as illustrated, or a left-hand turn, as seen towards the distal end of the lead 1. The coil is open, i.e. the intersection of the lead 1 with itself takes place on two levels, as will appear from FIG. 2, and the diameter or largest cross-section of the coil is adapted to prevent the portion of the lead 1 downstream of the coil to move outwards through the vena cava VCS. The coil 8 extends in the longitudinal direction of the lead 1, such that the line of intersection between the major plane of the coil and longitudinal planes of the lead 1 makes an angle with the longitudinal direction of the lead 1, which angle can be about 45°. The curved portion gently joins the coil 8 so that its centre of curvature lies on the same side of the lead 1 as the centre of curvature of the immediately connecting loop portion. The curvature of the portion 9 is such that by the intermediary of at least one auricle electrode said portion will be sure to contact, and be slightly urged against, the endocardium in the auricle AD, preferably following the general curvature of the endocardium, over a considerble distance $\alpha$, approximately from the mouth of the vena cava VCS in the auricle AD to the tricuspid valves TK, as will appear from FIG. 1, which is realised by a certain overdimensioning of the curved portion 9, such that the inherent resilience of the lead 1 realizes the above-mentioned urging.

The inner sheath 6 can be provided with the portions 8 and 9 by extrusion of a tube in a straight state, whereupon this tube before vulcanization is placed in a jig which is provided with release agent or passed onto a wire template of the same shape as that desired (see FIG. 1) for the lead portions 8, 9. The tube is then vulcanized in the jig or on the template. After insertion of the inner conductor 2 into the resulting tube which has been given the desired shape and which has optionally been expanded with the aid of gas to permit such insertion, and after passing of the tube onto the conductor 3 with the annular electrodes 5 attached thereto, the outer sheath 7 can be moulded over the outer conductor 3 between and beyond the electrodes 5.

After accomplished vulcanization the lead 1 is resiliently biased to the shape of the coil turn 8 and the curved portion 9, and after straightening the lead 1 can resume said desired curvature which is illustrated in FIGS. 1 and 2 and has a coil 8 and curved portion 9. The lead portions on both sides of these members 8, 9 are unbiased.

Straightening of the lead 1 has to be carried out before and during insertion of the electrodes 4 and 5 in the heart. To this end, a relatively stiff metal wire 10 is introduced into the central opening in the lead 1 defined by the conductor 2 and is moved all the way up to the electrode 4. Said wire simultaneously serves as straightening device for the loop or coil 8 and for the curved portion 9 and as a guide means for the ventricle electrode 4 for guiding it to the heart apex. After said electrode 4 has been brought into correct position, the lead being paid out simultaneously as the wire 10 is withdrawn through the puncture in the body vessel, for example one jugular vein, the wire 10 can be entirely withdrawn through said puncture. By reason of its spring bias described, the lead 1 is brought into the shape shown in FIGS. 1 and 2. With this shape of the lead 1, the auricle electrodes 5 positively bear against the endocardium of the auricle also when the heart is working, and the coil 8 prevents the part of the lead 1 located in the heart from moving out through the vena cava VCS, and results in the positive abutment of the electrode tip against the lower apex of the ventricle VD.

Thus, it will be appreciated that the coil 8 serves as a member absorbing the movements of the heart, and not transferring these movements to the other portions of the lead 1.

Being spring biased, the lead in the heart can take part in the movement of the heart simultaneously as the electrodes 4 and 5 remain in contact with the heart at the points illustrated in FIG. 1. The loop or coil 8 unloads the lead 1 from the stresses caused by the heart movements.

An annular magnet 11 can, if desired, be arranged in the annular space radially inside each ring electrode 5 or a number of said ring electrodes 5, as is illustrated in FIG. 3. Said magnet 11 can be caused to cooperate with a magnet placed on the outer side of the patient's body for fixation of the electrodes 5 to the myocardium until fibrin is precipitated onto the lead.

In a similar manner the lead 1 may contain a magnet also in the vicinity of its distal end to maintain the electrode 4 in contact with the myocardium in the ventricle VD until fibrin is precipitated, all in conformity with my U.S. Pat. No. 4,162,679.

The plurality illustrated of auricle electrodes is not necessary. It may very well be replaced by a few or even a single auricle electrode 5 in the curved portion 9. In that case, the electrode 5 is located at such a point of said portion that a positive contact is obtained with the endocardium in the right auricle AD.

The dimensions of the loop or coil 8 and the curved portion 9 are preferably determined on a model of the patient's heart. The following dimensional statements may, however, serve as a guide where the heart of an adult is concerned. Length $\alpha$ of curved portion $9 = 32$ mm, length $\beta$ from the distal end of the curved portion 9 approximately at the tricuspid valves TK to the distal end of the lead $= 85$ mm, diameter $\gamma$ of the approximately circular coil $8 = 22$ mm, distance $\delta$ between the mouth of the vena cava VCS in the auricle AD and the lowermost portion of the coil $= 15$ mm, distance of intersection $\epsilon$ at the coil $= 25$ mm, and total length of portions 8 and $9 = 130$ mm.

An alternative embodiment (not shown) of the lead 1 is a strip lead where the helical conductors 2 and 3 are placed in juxtaposition and each conductor is embraced by a sheath 6 and 7, with the exception that the conductor 3 comprises the auricle electrodes 5 which are devoid of sheaths. The conductors 2 and 3 may be enclosed together with the sheaths 6, 7 by a common catheter cover of a more rigid material than the sheaths 6 and 7 and movable in its longitudinal direction along the sheaths 6 and 7. The conductor 2 may be provided with a guide wire for guiding the electrode 4 into the right ventricle VD, and the sheath 7 for the conductor 3 is spring-biased, as described in the foregoing. The catheter cover serves the same straightening function as the wire 10 in the embodiment illustrated and can, after implantation in the heart, be withdrawn to restore the slackened shape of the sheath 7 and the conductor 3.

Instead of either sheath 6, 7 or the two sheaths 6 and 7 the electrical conductor or conductors 2, 3 can be biased to the desired shape (illustrated in FIG. 1) of the coil 8 and the curved portion 9, which helical conductors in the produced straight state are placed in a conventional manner, in a jig of the desired configuration for the lead 1, and heated, whereafter they are allowed to cool for obtaining memory. A lead 1 having an electrical conductor and of coil and/or loop form for contact with the auricle by means of auricle electrodes can of course be utilized without the aid of a ventricle electrode for solely auricle stimulation.

I claim:

1. An endocardial, implantable lead for connection with an implantable pacemaker, said lead comprising
   a predetermined portion of the lead (1) including
   a helical coil portion (8),
   and a curved portion (9) connected to said helical coil portion,
   an electrical conductor (3) in the lead in said predetermined portion,
   at least one electrode (5) connected to said electrical conductor and on said curved portion in a position adapted for contact with the inner wall of a heart auricle to transfer stimulating pulses to the heart or collect heart pulses from the heart,
   said curved portion being biased in its curved shape to bear against the inner wall of the heart auricle along a substantial portion of its length where said at least one electrode is located,
   said helical coil portion having a helical shape rising in the longitudinal direction of the lead to form an open coil in a manner to absorb compressive forces exerted on either side of the general plane of said coil portion.

2. A lead as claimed in claim 1, further characterized by the major plane of said coil portion forming an angle of substantially 45° with the longitudinal planes of the lead.

3. A lead as claimed in claim 1 further characterized in that the bias of said curved portion is generated by at least one of a tubular member (6, or 7) of an elastomer, which includes silicone rubber, which of said tubular members is concentric with said electrical conductor (3) but leaves said at least one electrode (5) free for contact with the inner wall of the auricle (AD).

4. A lead as claimed in claim 1, further characterized by an elongated means in releasable positive connection with said predetermined portion and having rigidity to counteract biased forces of said predetermined portion to permit insertion of said portion in the heart in a substantially straightened state.

5. A lead as claimed in claim 4 further characterized in that said conductor (3) is helically wound and that said elongated means (10) is a metal wire which is slidably arranged in an opening through said helically wound conductor (3).

6. A lead as claimed in claim 5, further characterized in that the lead contains a second electrical conductor (2) which extends past said first mentioned conductor by a length ($\beta$) which contains a second electrode (4) arranged to contact the inner wall of a heart ventricle (VD).

7. A lead as claimed in claim 6, characterized in that said conductors (2, 3) are coaxial and insulated by tubular members (6, 7), the auricle at least one electrode (5) being connected to the outer conductor (3).

8. A lead as claimed in any one of claims 6 or 7, characterized in that the metal wire (10) also serves as a guide for the ventricle electrode (4).

9. A lead as claimed in claim 1 characterized by said at least one electrode including additional electrodes, said electrodes being annular elements spaced apart along a substantial length of the curvature ($\alpha$) of said curved portion.

10. A lead as claimed in claim 1, further characterized in that the shape of said substantial portion of the length of the curvature of said predetermined portion generally corresponds to the curvature of the inner wall of the auricle (AD) in a longitudinal section thereof, from approximately the mouth of the superior vena cava (VCS) in the auricle to the tricuspid valves (TK).

11. A lead as claimed in claims 1 or 10 characterized in that the curvature comprises, in turn as viewed towards the distal end of the lead, a rising helical coil portion (8) of slightly larger transverse dimension than the transverse dimension of the mouth of the superior vena cava (VCS) in the auricle (AD), and a curved portion (9) gently connecting onto the coil and including the substantial portion of the length of curvature ($\alpha$) of said curved portion.

* * * * *